(12) United States Patent
Yoo

(10) Patent No.: US 6,299,955 B1
(45) Date of Patent: Oct. 9, 2001

(54) SUPPORTING BOARD FOR MOXIBUSTING IMPLEMENT OF LOESS

(76) Inventor: Tae Woo Yoo, 807, 1-Dong, Hanyang Apt., 32-5, Banpo-Dong, Seocho-Ku, Seoul (KR)

( * ) Notice: Subject to any disclaimer, the term of this patent is extended or adjusted under 35 U.S.C. 154(b) by 0 days.

(21) Appl. No.: 09/566,554

(22) Filed: May 8, 2000

(30) Foreign Application Priority Data

Feb. 25, 2000 (KR) .................................................. 00-5241

(51) Int. Cl.[7] .................................. B32B 7/06; B32B 3/10
(52) U.S. Cl. ...................... 428/40.1; 428/66.6; 428/137; 428/138; 604/291
(58) Field of Search .................................. 428/40.1, 138, 428/66.6, 137; 604/291

(56) References Cited

U.S. PATENT DOCUMENTS

| 5,549,960 | 8/1996 | Yoo . |
| 5,948,506 | 9/1999 | Yoo . |

Primary Examiner—Alexander S. Thomas
(74) Attorney, Agent, or Firm—Richard M. Goldberg

(57) ABSTRACT

A supporting board for moxibusting implement of loess including an upper board with a receiving hole in a center and applied adhesives at the upper surface; a lower board with a receiving hole in a center and applied adhesives at the lower surface; a filter paper between the two boards; and exfoliation papers attached to the boards.

2 Claims, 10 Drawing Sheets

F I G 13
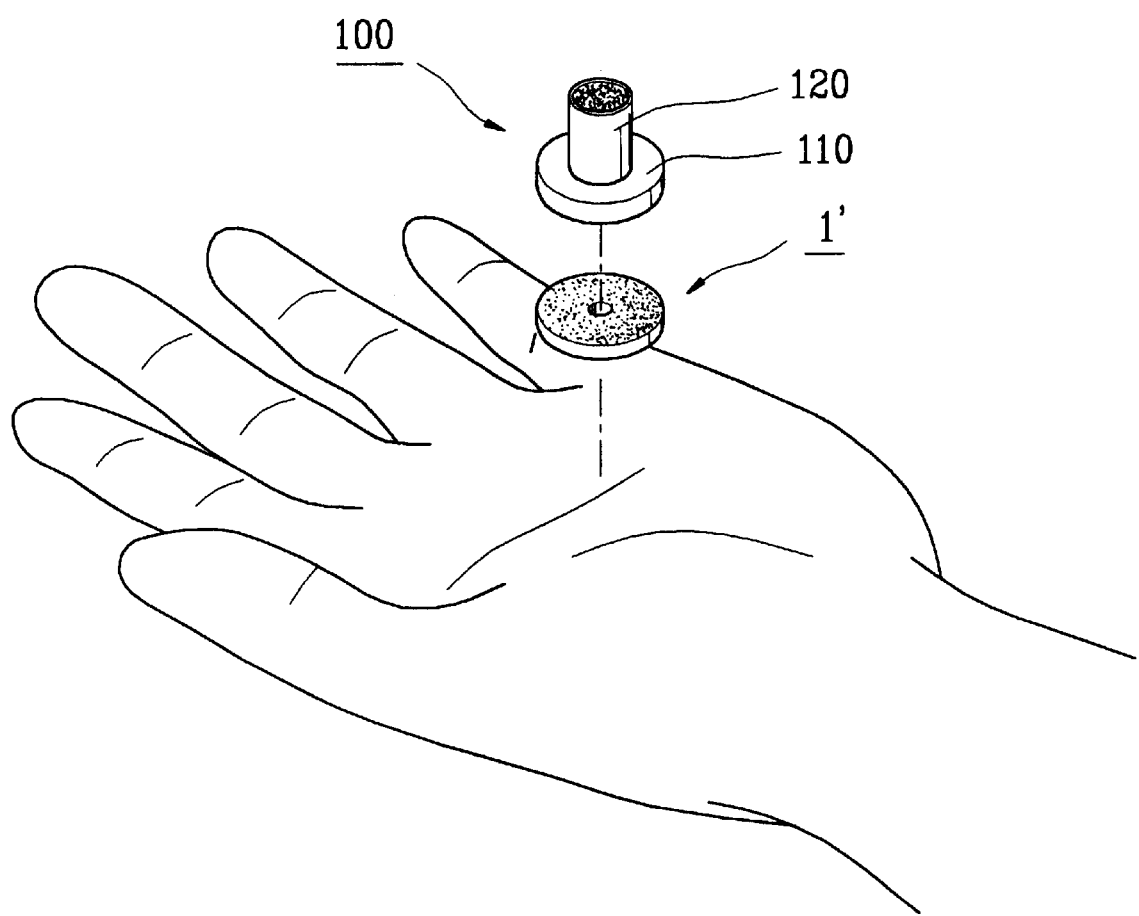

SUPPORTING BOARD FOR MOXIBUSTING IMPLEMENT OF LOESS

BACKGROUND OF THE INVENTION

1. Field of the invention

The present invention relates to a supporting board for a moxibusting implement of loess and more particularly to a supporting board for a moxibusting implement of loess including an upper board with a receiving hole in a center and applied adhesive at the upper surface; a lower board with a receiving hole in a center and applied adhesive at the lower surface; a filter paper between the two boards; and exfoliation papers attached to the boards. The present invention provides economical effect due to a simple manufacturing process and strong moxacautery effect and absorbing effect of far-infrared radiation heat produced from loess.

2. Description of the Prior Art

In general, a traditional moxibusting implement is manufactured by adhering a supporting board comprising an upper board with a receiving hole, filter paper, a lower paper and exfoliation paper to a loess board with a moxa attached by adhesives in a regular sequence. The moxibusting implement was attached to a supporting board by handiwork and therefore the manufacturing process required much time and cost. Also, during operation on a person, a supporting board of loess is removed from the attached exfoliation paper, is attached to the spot of a body and ignited. If a further moxibusting is required after a complete combustion of the first moxibusting implement, the first supporting board has to be replaced by a new one.

SUMMARY OF THE INVENTION

A supporting board for a moxibusting implement of loess according to the invention was designed to solve the problems as described above. The object of the present device is to provide a more cost-effective moxibusting implement by reducing manufacturing process such as attaching a supporting board to the bottom of a moxibusting implement. During operation on a person, remove the exfoliation paper of the supporting board for the moxibusting implement is removed, the moxibusting implement of loess is adhered to the supporting board and then the moxa is ignited. The moxa is oxidated and smoke flows downwardly through the support board of loess. Moxa resin is removed and far-infrared radiation heat produced from the supporting board of loess is absorbed into the skin through a receiving hole.

The present moxibusting implement is made for possible continuing moxibustings just by attaching new moxibusting implements to adhesive on the surface of the upper board of the supporting board after a complete combustion. Therefore, the present invention can obtain convenient and economical effects.

BRIEF DESCRIPTION OF THE DRAWINGS

Other objects and features of the present invention will be hereinafter explained in detail with reference to the accompanying drawings, wherein:

FIG. 13 is an exemplary status view of an operation.

DESCRIPTION OF THE PREFERRED EMBODIMENTS

Figure 1:
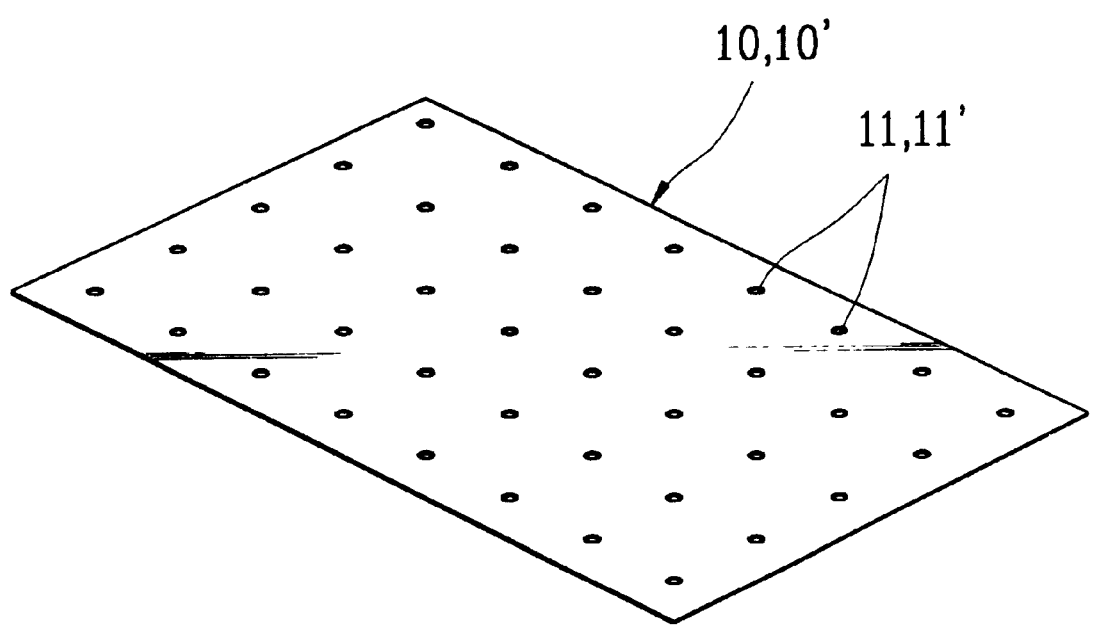
FIG. 1 is a perspective view of a manufacturing process of an upper and a lower board according to the present invention.

The supporting board 1 for the moxibusting implement of loess is comprised of an upper board 10 with a receiving hole 11 in a center and applied adhesive 12 at the upper surface; a lower board 10' with a receiving hole 11' in a center and applied adhesive 12' at the lower surface; a filter paper 20 between the two boards; and exfoliation papers 30, 30' attached to the adhesive sides of the boards.

Numeral 200 refers to a cutting line for the supporting boards 1.

Figure 2:
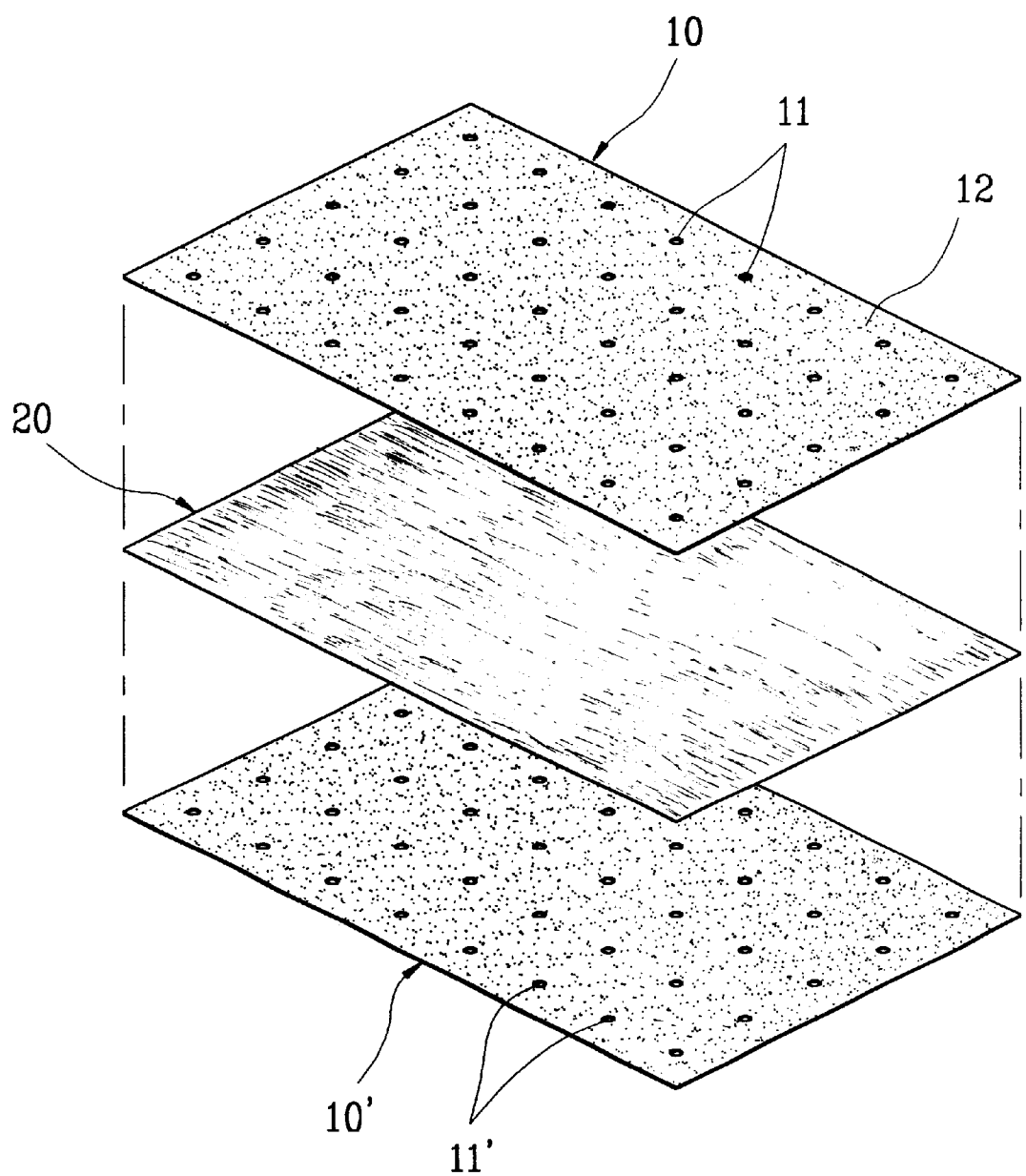
FIG. 2 is a perspective view of a process inserting a filter paper between the upper and the lower boards.
Figure 3:
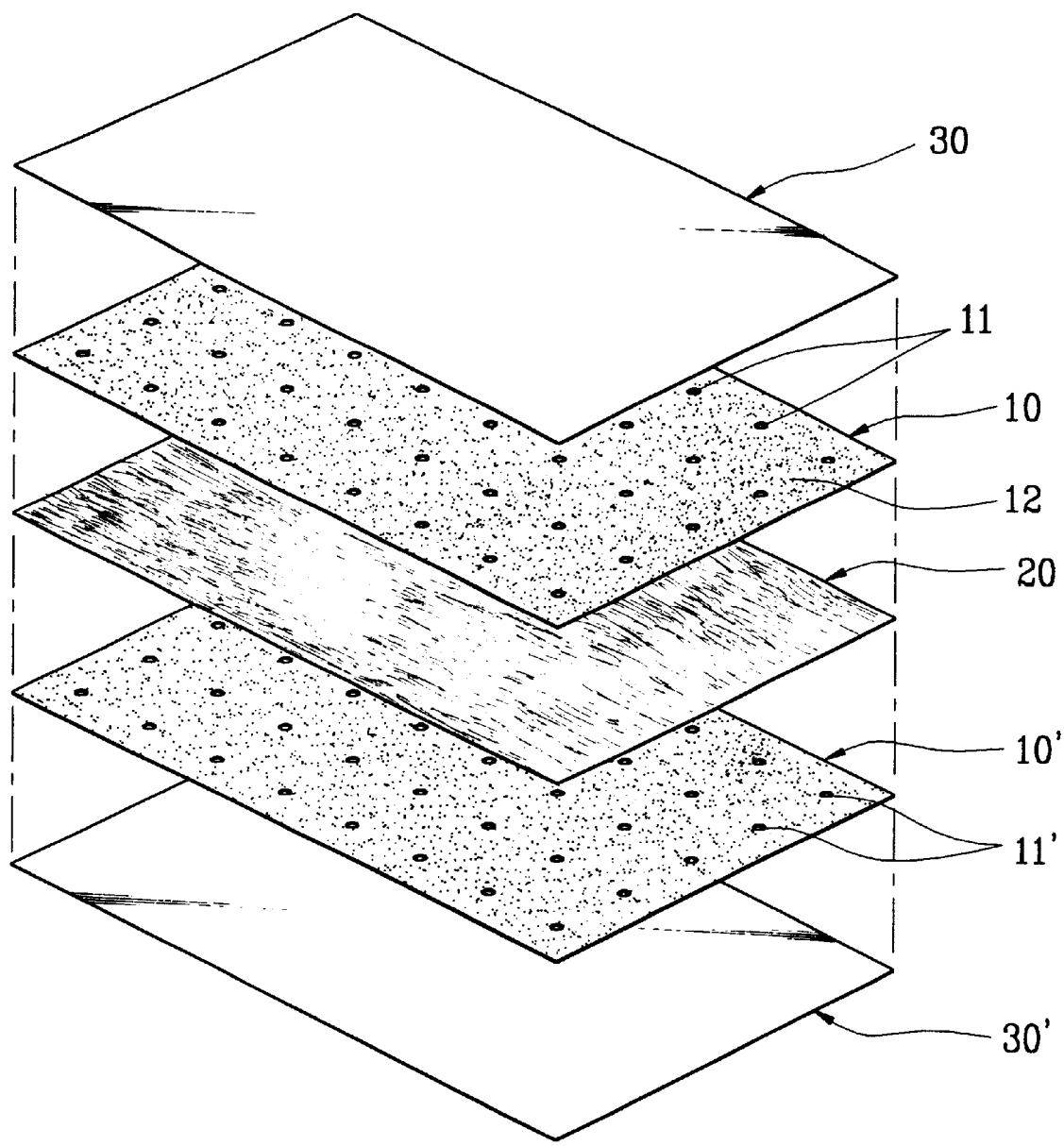
FIG. 3 is a perspective view of a process inserting a filter paper between the upper and the lower boards and attaching exfoliation papers at an upper surface of an upper board and a lower surface of a lower board, respectively.
Figure 4:
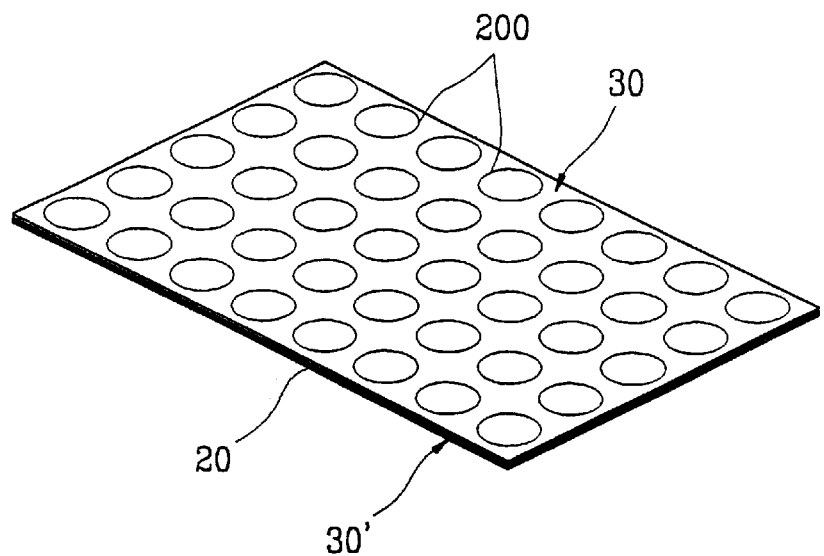
FIG. 4 is a perspective view of cut supporting boards according to the invention.
Figure 5:
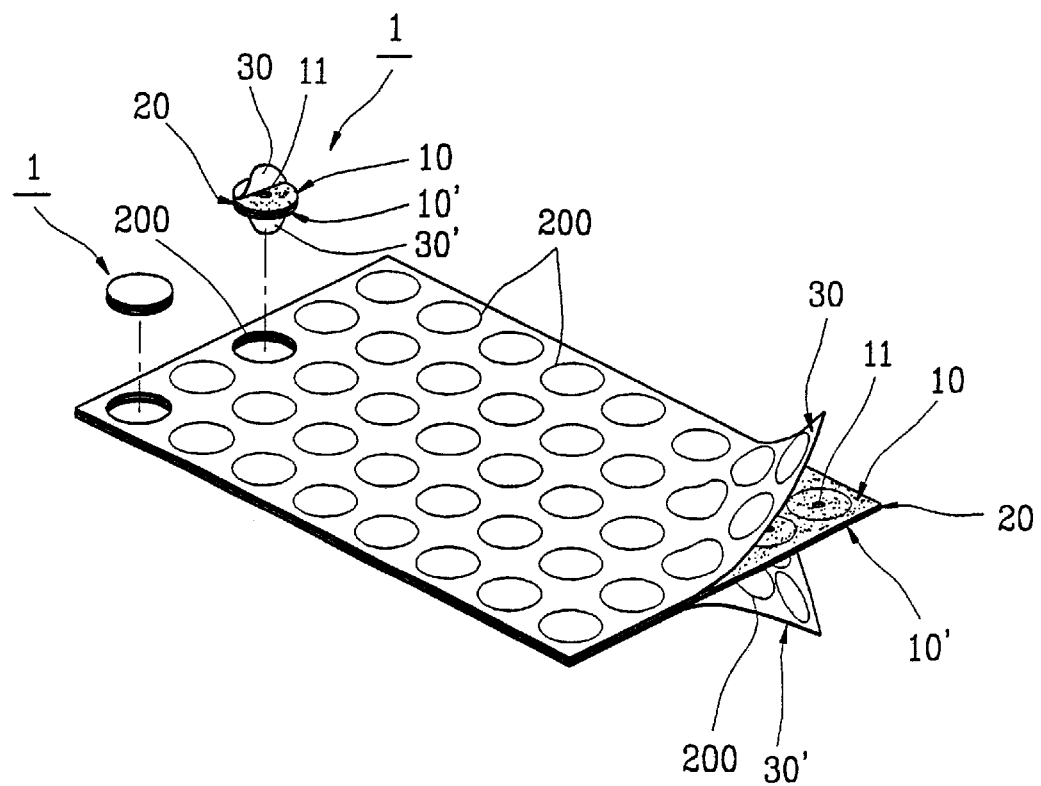
FIG. 5 is an exemplary status view of detaching supporting boards one by one according to the invention.
Figure 6:
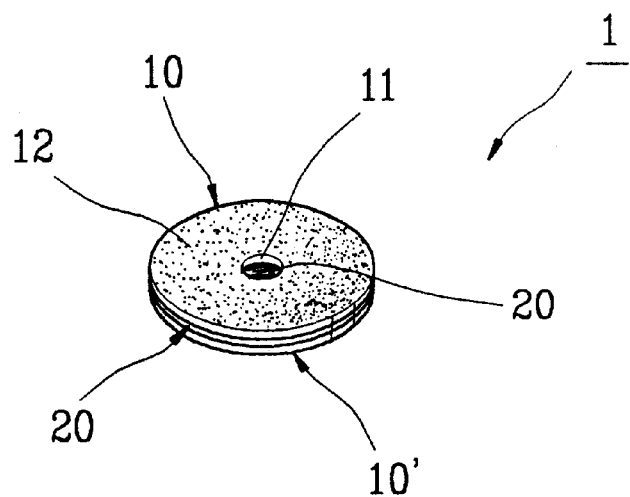
FIG. 6 is a perspective view of a supporting board from which an exfoliation paper is removed.
Figure 7:
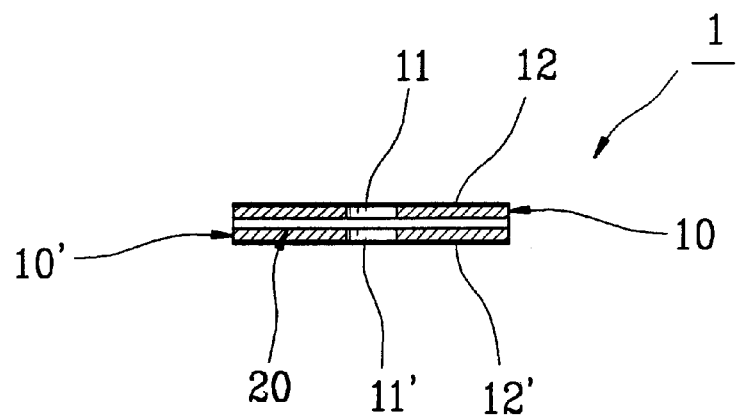
FIG. 7 is a cross-sectional view of FIG. 6.
Figure 8:
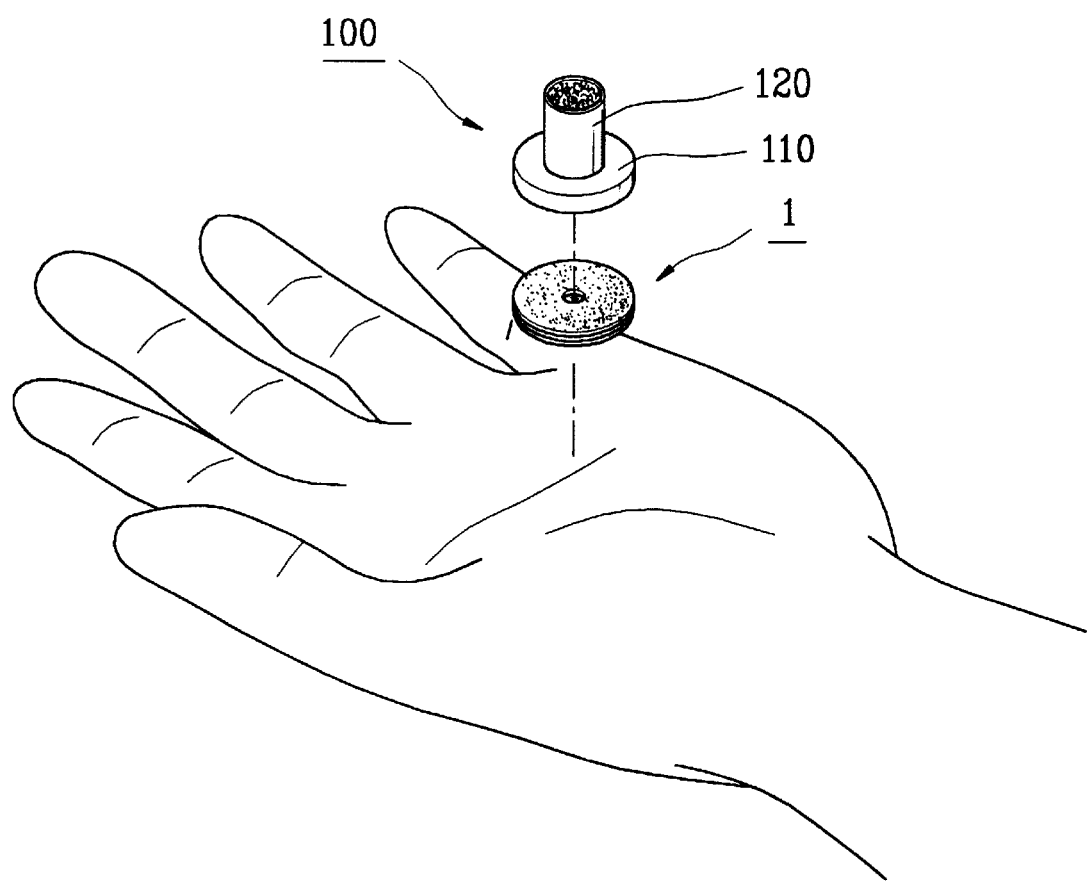
FIG. 8 is an exemplary status view of operating the present invention.
Figure 9:
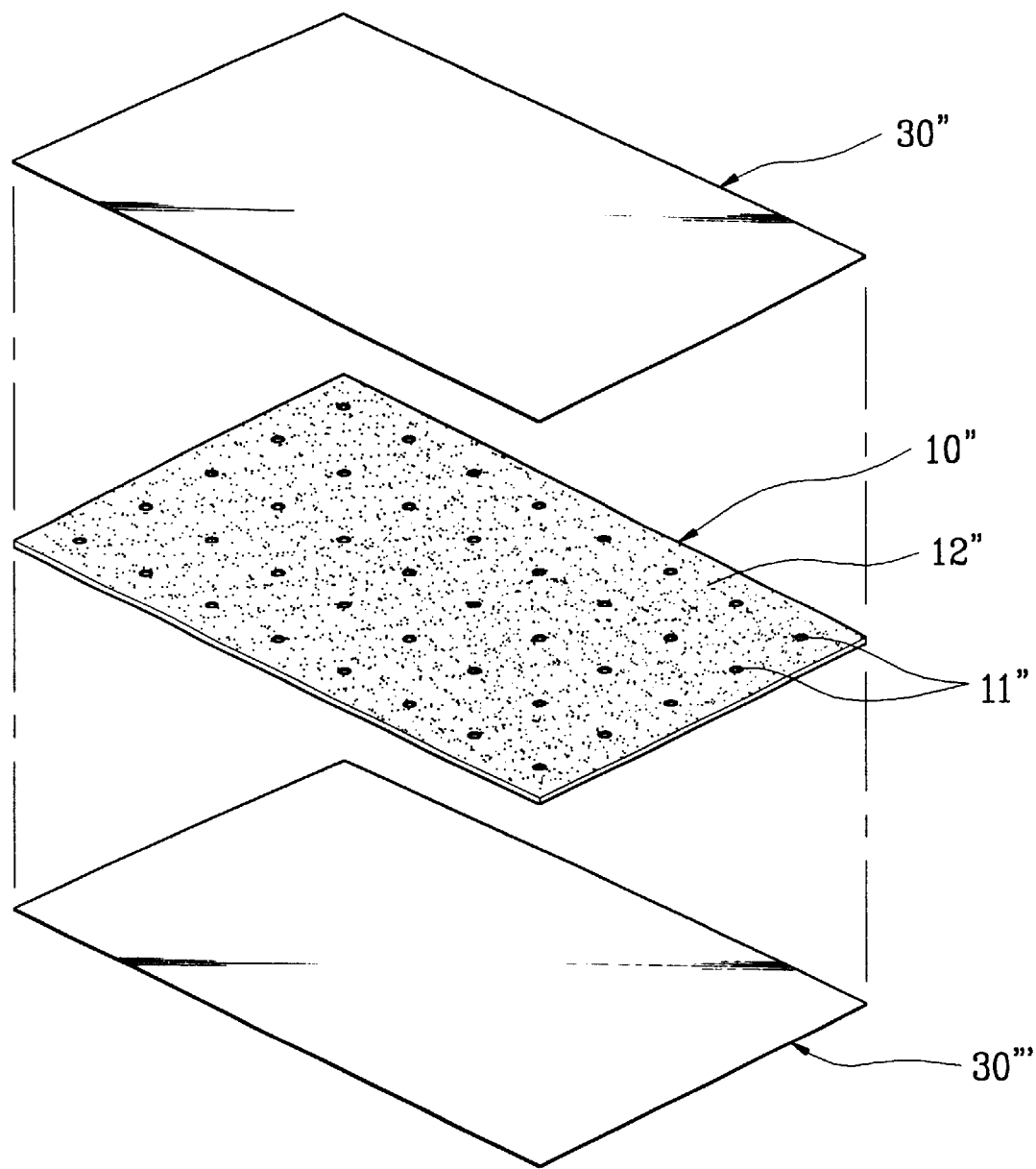
FIG. 9 is a perspective view of a process attaching an exfoliation paper to a paper board.
Figure 10:
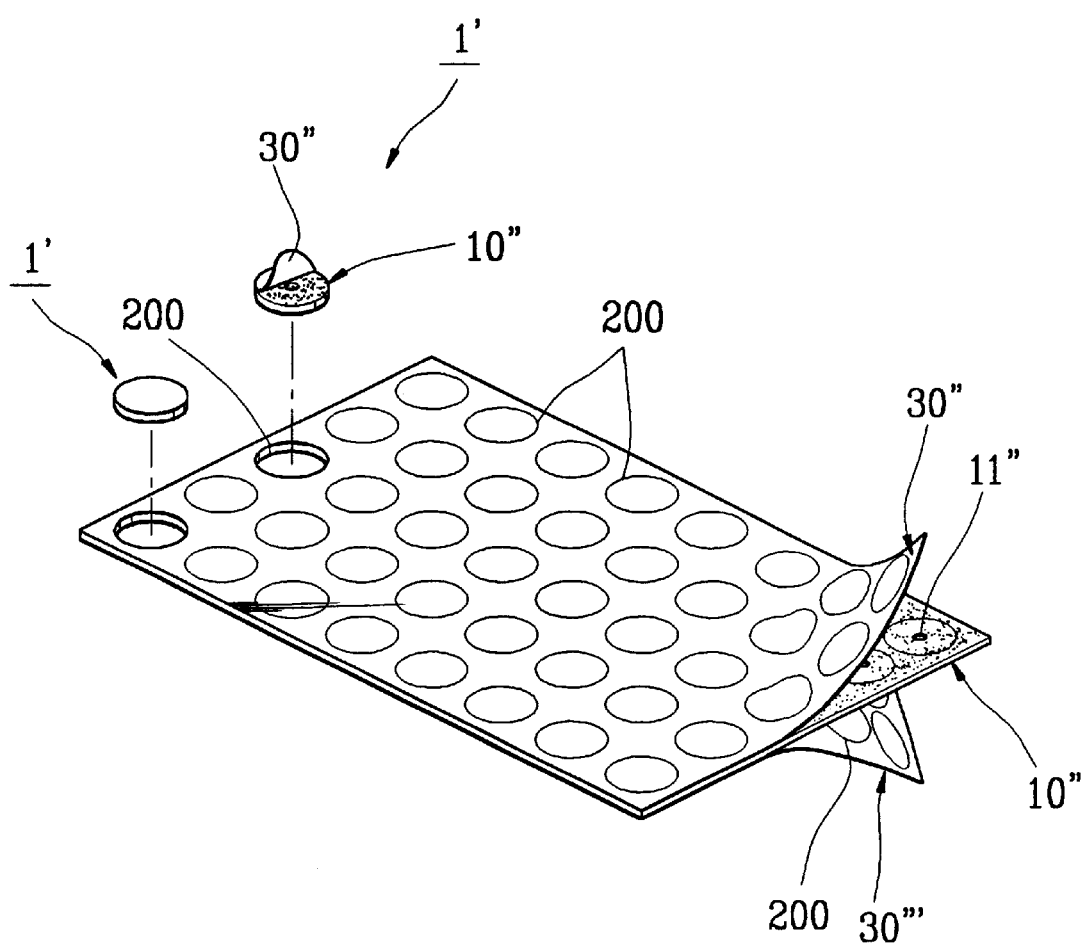
FIG. 10 is an exemplary status view of detaching supporting boards one by one.

As shown in FIG. 1, the supporting board 1 for a moxibusting implement of loess according to the present invention has a plurality of receiving holes 11, 11' on the same-sized upper and lower boards. As shown in FIG. 2, the filter paper 20 is inserted between the upper and the lower boards 10, 10' with receiving holes 11, 11'. As shown in FIG. 3, the upper and the lower boards 10, 10' are applied with adhesives 12, 12' and then the exfoliation papers 30, 30' are attached on the upper surface of the upper board and the lower surface of the lower board, respectively. As shown in FIG. 4, a cutter cuts out the supporting boards 1 along lines 200 around receiving holes as a center. As shown in FIG. 5, the supporting boards 1 for the moxibusting implement of loess are detached one by one. As shown in FIG. 8, during operation a person, the exfoliation paper 30' is removed from the supporting board 1 for the moxibusting implement, and adhered to a spot of a body by adhesive 12' of the lower board. The exfoliation paper 30 is removed from the supporting board 1 for the moxibusting implement and the moxibusting implement of loess 100 is adhered to the adhesive 12 of the upper surface of the upper board 10, and then the moxa 120 is ignited. When the moxa is completely oxidated, the supporting board of loess 110 is removed, and another moxibusting implement of loess 100 is ahdered to the adhesive 12 of the upper surface of the upper board 10. A continuing moxibusting operation is conducted.

Figure 11:
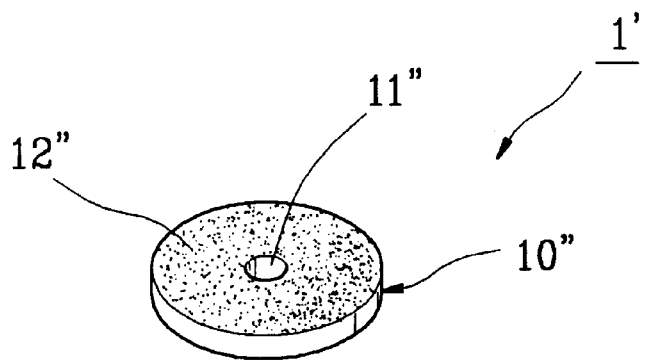
FIG. 11 is an exemplary status view of removing exfoliation papers.
Figure 12:
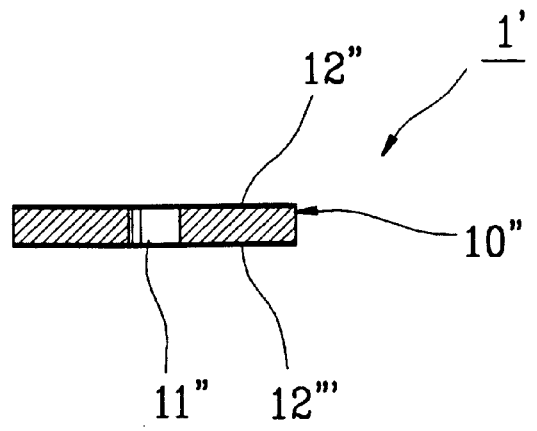
FIG. 12 is a cross-sectional view of FIG. 11.

As shown in FIGS. 11 and 12, the supporting board for a moxibusting implement of loess, includes a paper board 10" with a receiving hole 11" and applied with adhesives 12', 12'" and the exfoliation papers 30", 30'". As shown in FIG. 13, the supporting board for a moxibusting implement of loess is attached to the spot of a body and the exfoliation paper 12" is removed. Then, the moxibusting implement 100 is replaced with a new one. As mentioned above, the present invention provides an enhanced continuing moxibusting effect.

What is claimed is:

1. A supporting board for a moxibusting implement of loess, comprising:

an upper board with a receiving hole in a center thereof and an upper surface;

an adhesive applied to the upper surface of the upper board;

a lower board with a receiving hole in a center thereof and a lower surface;

an adhesive applied to the lower surface of the lower board;

a filter paper between the upper and lower boards; and exfoliation papers attached to the upper surface of the upper board and the lower surface of the lower board by said adhesives.

2. A supporting board according to claim 1, wherein said supporting board has a disk shaped configuration with the receiving holes in a center of the disk shaped configuration.

* * * * *